(12) United States Patent
Chow et al.

(10) Patent No.: US 11,172,866 B2
(45) Date of Patent: Nov. 16, 2021

(54) PELVIC MUSCLE REHABILITATION FOR TREATING URINARY INCONTINENCE

(71) Applicant: Children's Medical Center Corporation, Boston, MA (US)

(72) Inventors: Jeanne Chow, Boston, MA (US); Carlos Estrada, Brookline, MA (US); Michael K. Dempsey, Groton, MA (US)

(73) Assignee: Children's Medical Center Corporation, Boston, MA (US)

(*) Notice: Subject to any disclaimer, the term of this patent is extended or adjusted under 35 U.S.C. 154(b) by 14 days.

(21) Appl. No.: 16/333,780

(22) PCT Filed: Sep. 27, 2017

(86) PCT No.: PCT/US2017/053734
§ 371 (c)(1),
(2) Date: Mar. 15, 2019

(87) PCT Pub. No.: WO2018/064172
PCT Pub. Date: Apr. 5, 2018

(65) Prior Publication Data
US 2019/0246937 A1    Aug. 15, 2019

Related U.S. Application Data

(60) Provisional application No. 62/400,999, filed on Sep. 28, 2016.

(51) Int. Cl.
*A61B 5/391*    (2021.01)
*A61B 5/00*    (2006.01)
(Continued)

(52) U.S. Cl.
CPC ............ *A61B 5/391* (2021.01); *A61B 5/0002* (2013.01); *A61B 5/208* (2013.01); *A61B 5/296* (2021.01);
(Continued)

(58) Field of Classification Search
CPC . A61B 5/0002; A61B 5/04882; A61B 5/0492; A61B 5/208; A61B 5/486; A61B 5/6804; A61B 5/6808
See application file for complete search history.

(56) References Cited

U.S. PATENT DOCUMENTS

2002/0019615 A1   2/2002  Roe et al.
2007/0255176 A1*  11/2007 Rondoni ................ A61B 5/204
                                                 600/573
(Continued)

FOREIGN PATENT DOCUMENTS

WO    WO0000083    1/2000

OTHER PUBLICATIONS

PCT International Preliminary Report on Patentability in International Appln. No. PCT/US2017/53734, dated Apr. 2, 2019, 9 pages.
(Continued)

*Primary Examiner* — George Manuel
(74) *Attorney, Agent, or Firm* — Fish & Richardson P.C.

(57) ABSTRACT

The systems and methods described herein combine both moisture and electromyograph (EMG) sensors in a single wearable garment, along with a suitable output device such as a "smart" mobile device or computer, to provide users with new and useful feedback that can significantly improve incontinence symptoms. The EMG provides feedback to the user specifically regarding the quality of pelvic floor muscle contractions, while the moisture sensor provides feedback about the "end result" of the subjects' incontinence. Each measurement device alone can also provide useful informa-
(Continued)

tion and feedback to different population groups. Combining these two measurements provides unprecedented data to enhance the subjects' therapy in managing urinary incontinence.

20 Claims, 8 Drawing Sheets

(51) Int. Cl.
    *A61B 5/20*     (2006.01)
    *A61B 5/296*     (2021.01)

(52) U.S. Cl.
    CPC .......... *A61B 5/6804* (2013.01); *A61B 5/6808* (2013.01); *A61B 5/486* (2013.01)

(56) References Cited

U.S. PATENT DOCUMENTS

| | | |
|---|---|---|
| 2010/0114046 A1 | 5/2010 | Ales et al. |
| 2015/0182161 A1 | 7/2015 | Mananas et al. |
| 2016/0095758 A1 | 4/2016 | Haire et al. |
| 2016/0174866 A1 | 6/2016 | Chan |

OTHER PUBLICATIONS

PCT International Search Report and Written Opinion in International Appln. No. PCT/US2017/53734, dated Jan. 12, 2018, 10 pages.

\* cited by examiner

PELVIC MUSCLE REHABILITATION FOR TREATING URINARY INCONTINENCE

CLAIM OF PRIORITY

This application is a 371 U.S. National Phase Application of PCT/US2017/053734, filed on Sep. 27, 2017, which claims priority to U.S. Patent Application Ser. No. 62/400,999, filed on Sep. 28, 2016, the entire contents of which are hereby incorporated by reference.

TECHNICAL FIELD

This invention relates to systems and methods for monitoring and quantification of pelvic biofeedback.

BACKGROUND

At least 25 million Americans suffer from various forms of urinary incontinence, such as stress incontinence, the treatment of which represents a $3 billion annual market in 2016. The standard of care for 80% of the patients (20 million people) is a regimen of Kegel exercises ("Kegels"), which strengthen pelvic floor muscles. However, Kegels are "blind exercises" in that patients do not know if they are doing the Kegels properly or if they are making progress. As a result, many patients prematurely abandon Kegels. Pelvic floor muscle therapy (PFMT), or electromyography (EMG)-guided Kegels, is one current solution, but is often invasive (using intravaginal or intrarectal probes) and generally limited to use in highly specialized centers. PFMT is therefore underutilized. In addition, due to the intravaginal nature of many current solutions, they are not appropriate for men and children. In addition to patients with urinary incontinence, PFMT has been used to prevent or minimize incontinence in men prior to prostate surgery and in pregnant women, and has been used to treat sexual dysfunction in both men and women.

SUMMARY

The new systems and methods described herein are based, at least in part, on the discovery that combining both moisture and electromyograph (EMG) sensors in a single wearable device, along with a suitable output device such as a "smart" mobile device or computer, can provide users with new and useful feedback that can significantly improve incontinence symptoms. The EMG provides feedback to the user specifically regarding the quality (duration, intensity, etc.) of the pelvic floor muscle contractions, while the moisture sensor provides feedback about the "end result" of the subjects' incontinence: how much urine they are leaking. Combining these two measurements provides unprecedented data to enhance the subjects' therapy.

Additionally, these sensors are non-invasive, and so are more appealing to most users. In general, currently available portable or mobile EMG-based pelvic floor muscle therapy (PFMT) treatments require vaginal or rectal insertion of a device, which is avoided by the systems described herein. Additionally, there are few, if any, products currently designed for men, and the new systems described herein are highly effective for men as well as women and children.

The systems described herein utilize noninvasive surface EMG electrodes to provide feedback on PFMT exercises, as well as novel moisture detection systems to provide information that quantifies the degree of incontinence. The systems make wearable, noninvasive PFMT readily available to any user with access to a smart mobile device or computer, bringing the treatment of urinary incontinence by PFMT from solely at specialized clinics to the user's home or any convenient location (such as the subway, work, home, etc.). The systems can also integrate into the clinical environment. This convenience and portability of these systems allows the exercises to occur more frequently and easily. The systems combine wearable superficial sensors and a smartphone application to allow users to assess, track, and record progress with PFMT.

In one aspect this disclosure relates to wearable devices to diagnose, treat, and/or manage incontinence. The devices include an electromyography (EMG) sensor arranged within a garment to measure contraction of a pelvic floor muscle of the wearer of the garment, and a moisture sensor arranged within the garment for measuring a level of urine voided by the user as a function of time. These devices can cause the EMG sensor to contact the user's skin sufficiently to obtain a measurement of a contraction of a pelvic floor muscle. The EMG sensor and moisture sensor can be attached to a substrate.

In another aspect, this disclosure relates to systems to diagnose, treat, and/or manage incontinence. The systems include a wearable device, e.g., a reusable garment with a disposable pad as described herein and a display device that receives data from the wearable device. The wearable devices can include a reusable component such as a microprocessor and Bluetooth radio and wires attached to the microprocessor and Bluetooth radio or sensor. The reusable component can be underwear, a diaper, or shorts, or the reusable component can be removably attachable to the garment. The wearable devices can also include a consumable component such as an absorbent component.

The systems can further include a software application configured to receive data communicated, e.g., automatically receive, from the wearable device and to display data to the user. The software applications can be further configured to automatically send and receive data to and from an external system, such as one maintained by a healthcare practitioner.

In another aspect, the disclosure relates to methods of diagnosing, treating, and/or managing incontinence. These methods include providing a disposable component including an electromyography (EMG) sensor configured to measure contraction of a pelvic floor muscle of a wearer of the disposable component and a moisture sensor for measuring a level of urine voided by the wearer, detecting a signal from the EMG sensor and/or the moisture sensor, and saving an output based on the signal from the EMG sensor and/or the moisture sensor.

In these methods, the output can include data corresponding to pelvic floor muscle exercisers performed by the user. The output can include a number of incontinence episodes detected or a volume of fluid detected. The methods can further include displaying the output on a screen, e.g., on a smart phone, laptop, or computer monitor. The methods can include transmitting data to outside systems for remote diagnosis, storage, and treatment.

In some implementations, these systems include a moisture sensor. Such a moisture sensor is noninvasive, and can provide useful information to patients who are not yet incontinent or who are determining if they are incontinent.

In another aspect, the disclosure relates to methods of diagnosing, treating, and/or managing weak pelvic muscles in a patient. The methods include providing a disposable component configured to be attached to a garment that when worn places an electromyograph (EMG) sensor that measures contraction of a pelvic floor muscle of the patient, detecting a signal from the EMG sensor, and saving an output based on the signal from the EMG sensor and/or the moisture sensor. The methods can further include displaying the output on a display device.

In another aspect, the disclosure relates to methods of diagnosing, treating, and/or managing incontinence in a patient. The methods include providing a disposable component configured to be attached to the patient, the disposable component comprising a moisture sensor, detecting a signal from the moisture sensor, and saving an output based on the signal from the moisture sensor. These methods can further include determining, from the signal detected from the moisture sensor, a volume of urine voided by the patient, or a number of times the patient has voided. They can also include displaying the output on a display device.

In some implementations, these systems include EMG sensors. Such an EMG sensor system is noninvasive, and can provide useful information to patients who experience disorders other than incontinence, for example, patients experiencing sexual dysfunction and pelvic pain.

The new systems and methods provide several advantages. Users are able to receive immediate feedback on how they are performing prescribed exercises. The systems described herein are non-invasive, not requiring vaginal or rectal insertion of a device required by other EMG-based PFMT treatments. The systems are readily adaptable to women as well as men, which is particularly advantageous as men with incontinence are often underserved. The systems are also adaptable to children. The systems are also able to provide information that quantifies degree of incontinence. Because the systems are wearable and discreet, the user can perform the exercises at home, or any place or time that is convenient to the user. In addition, both the user and a healthcare provider can assess, track, and record progress of the user's PFMT using the new systems. In addition, users' data may be applied to machine learning algorithms to provide individualized custom coaching programs.

"Electromyography" or "EMG" refers to an electrodiagnostic medicine technique for evaluating and recording the electrical activity produced by skeletal muscles.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

Like reference symbols in the various drawings indicate like elements.

DETAILED DESCRIPTION

This disclosure is based, at least in part, on the discovery that the use of either one or both of a moisture sensor and an electromyography (EMG) sensor on a wearable device in conjunction with an application on a smart mobile device or computer achieves significantly beneficial results for both pediatric and adult male and female users to improve their incontinence symptoms by performing pelvic floor muscle therapy (PFMT) without the need for invasive devices. The new systems and methods provide the user with feedback on how they are performing the exercises, and the history of the performed exercises can be stored for viewing by the user and/or a healthcare practitioner.

The novel systems described herein utilize noninvasive surface patch EMG electrodes and moisture sensors that together with new software provide information that quantifies the degree of incontinence and the level of improvement over time and are readily adaptable to both women and men. Rather than requiring clinic visits, the novel system makes wearable, noninvasive PFMT readily available to any user with access to a smart mobile device or computer. The systems combine wearable superficial sensors and a software application to allow users to assess, track, and record progress with PFMT. The systems described herein provide an easy to wear and use format that allow people to both monitor and treat their incontinence. In addition, users' data may be applied to machine learning algorithms to provide custom individualized coaching programs.

Methods of Making Noninvasive Wearable Pelvic Systems

Figure 1:
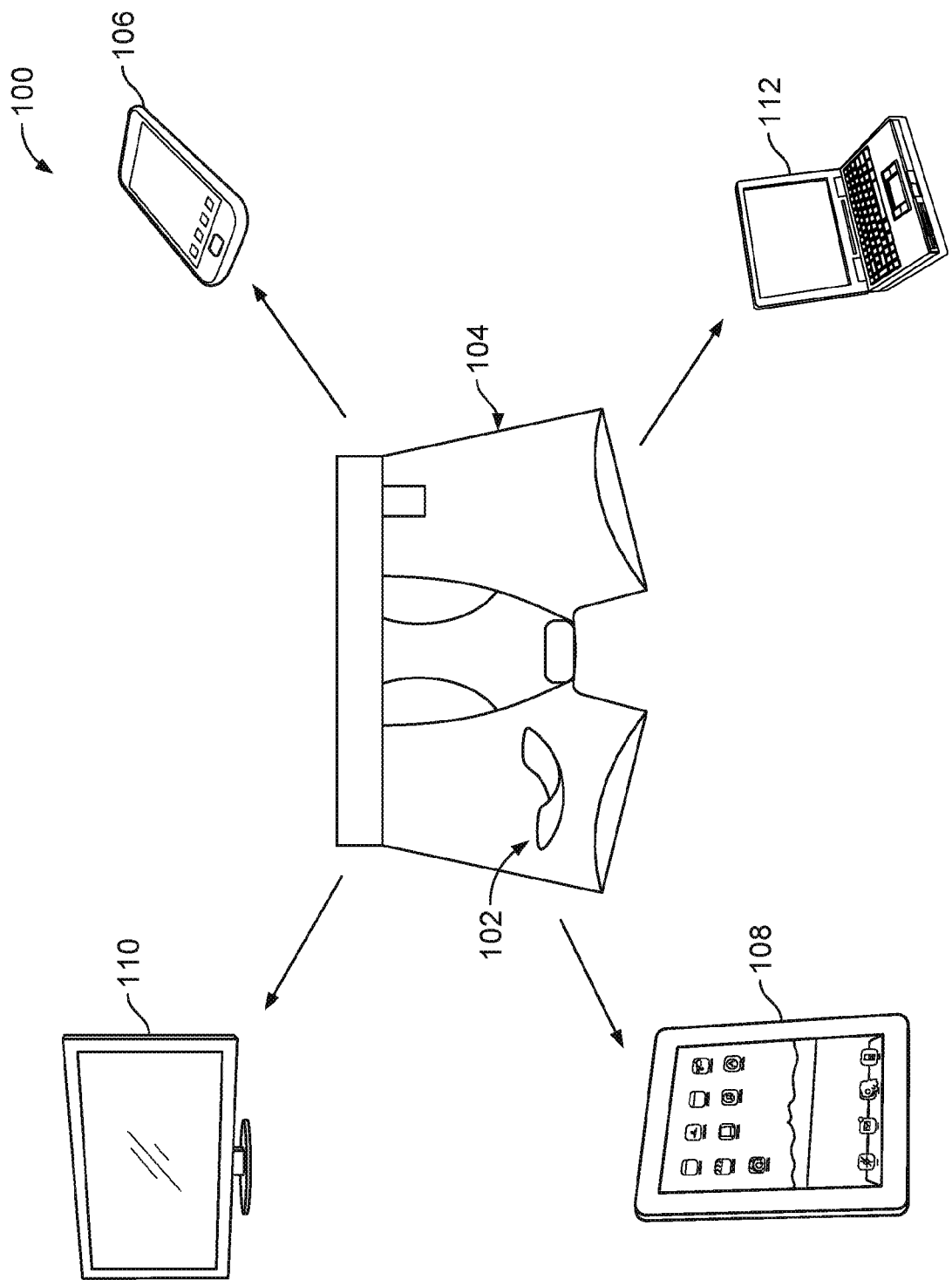
FIG. 1 is a schematic diagram of an example of a system as described herein for performing and monitoring noninvasive pelvic floor muscle therapy.

FIG. 1 illustrates a collection of potential systems, platforms, devices, etc. that are designed to interact with noninvasive wearable system 100 that includes noninvasive system sensors 102 that are attached to a garment 104. The garment 104 can be, for example, an undergarment, such as male underwear, female underwear, or a diaper. The garment 104 can also be sport shorts, such as bike, compression, or exercise shorts, which can be worn without an undergarment. Content generated by the noninvasive system sensors 102 can be communicated with and displayed on various devices including hand-held devices such as a cellular telephone 106, a tablet computing device 108 or other smart device, etc., that are programed to receive and display the data. Similarly, a television 110 or different types of computing devices (e.g., a laptop computer system 112) can also be programed to receive and display the data. These type of computing devices can be located near the user, or can be part of specialized systems used by healthcare providers.

Figure 2:
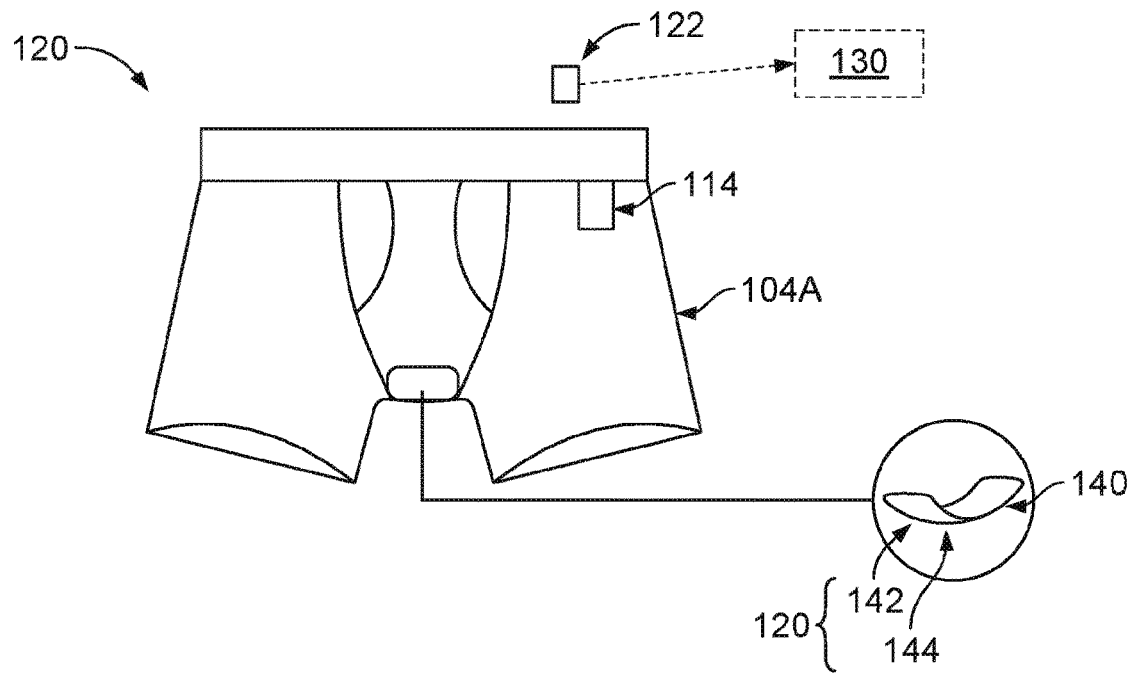
FIG. 2 is a schematic diagram of an exemplary wearable system for performing and monitoring noninvasive pelvic floor muscle therapy designed for use by males.

FIG. 2 shows a male wearable noninvasive system 120 that integrates consumable or disposable components with durable or reusable components. The durable components used with system 120 include: 1) a wearable and washable male undergarment 104A that can hold wiring, 2) a microprocessor and a radio or other wireless transmission unit (such as those that comply with the Bluetooth, WiFi, or other appropriative communications standard) integrated into a module 122, and 3) a software application 130 that processes data into visual elements that represent muscle activity and quantification of incontinence and that communicates with module 122. The module 122 can be insertable into a pocket 114 of the garment 104A, or fastenable to the garment 104A, for example by a clip that attaches the module 122 to a band of the garment 104A. The software application 130 can be located on the cellular telephone 106 shown in FIG. 1, a tablet computing device 108, or other smart device that has a receiver portion of the microprocessor and/or radio unit that communicates with the insertable radio or wireless transmission module 122.

The consumable component that attaches to the undergarment 104A is a novel removable pad 140 adapted to male anatomy with noninvasive system sensors 102. The noninvasive system sensors 102 can include surface EMG sensors 142 to record pelvic muscle activity, moisture sensors 144 to quantify degree of incontinence, or advantageously both EMG sensors 142 and moisture sensors 144. Either or both of these types of sensors can integrated into removable pad 140, either in proximity to each other or somewhat displaced from each other (for example, one located on a front of the pad 140 and the other located on the back of the pad 140).

In some embodiments, the removable pad 140 can be separated from the garment 104A, the garment 104A (whether underwear, shorts or other garment), being fit to the user's body to keep the EMG sensors 142 in as full contact as possible with the wearer's skin. Alternatively, the consumable component could be permanently integrated into the garment, e.g., a disposable or reusable undergarment.

Figure 3:
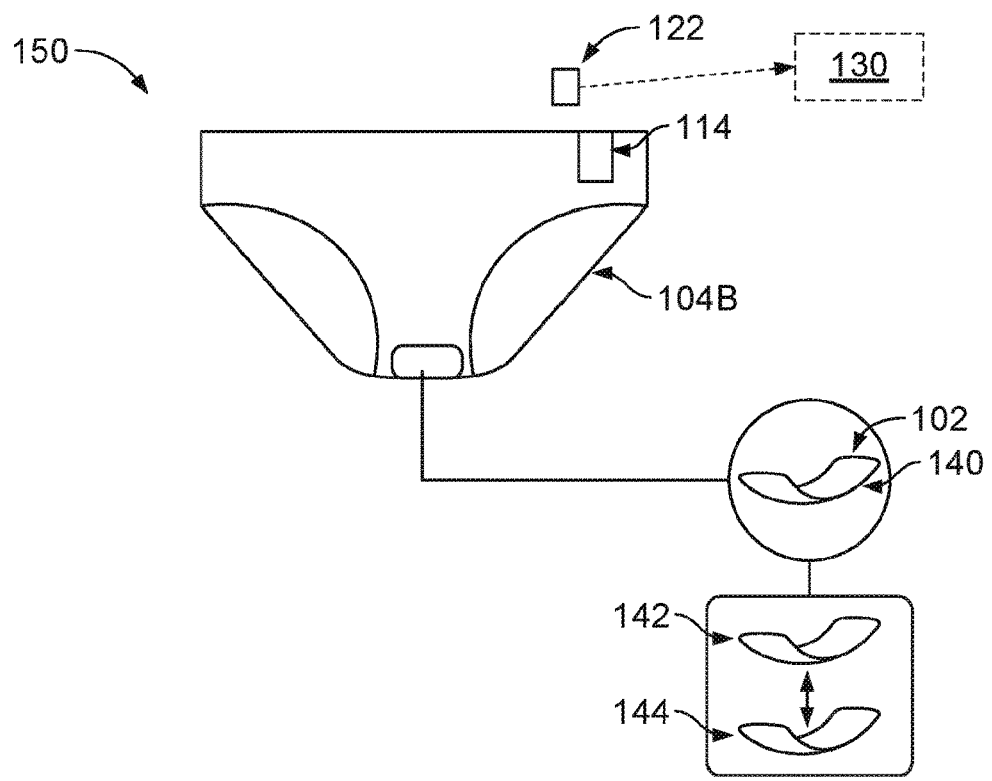
FIG. 3 is a schematic diagram of an exemplary wearable system for performing and monitoring noninvasive pelvic floor muscle therapy designed for use by females.

FIG. 3 shows a female wearable PFMT system 150 that integrates consumable or disposable components with durable or reusable components. The durable components used with system 120 include: 1) a wearable and washable male undergarment 104B that can hold wiring, 2) a microprocessor and a radio or other wireless transmission unit (such as those that comply with the Bluetooth, WiFi, or other appropriative communications standard) integrated into a module 122, and 3) a software application 130 that processes data into visual elements that represent muscle activity and quantification of incontinence and that communicates with module 122. The module 122 can be insertable into a pocket 114 of the garment 104B, or fastenable to the garment 104B, for example by a clip that attaches the module 122 to a band of the garment 104B. The software application 130 can be located on the cellular telephone 106 shown in FIG. 1, a tablet computing device 108, or other smart device that has a receiver portion of the microprocessor and/or radio unit that communicates with the insertable radio or wireless transmission module 122.

The consumable component that attaches to the undergarment 104B is a novel removable pad 140 adapted to female anatomy with noninvasive system sensors 102. The noninvasive system sensors 102 can include surface EMG sensors 142 to record pelvic muscle activity, moisture sensors 144 to quantify degree of incontinence, or advantageously both EMG sensors 142 and moisture sensors 144. Either or both of these types of sensors can integrated into removable pad 140, either in proximity to each other or somewhat displaced from each other (for example, EMG sensor 142 located on a separate layer of the pad 140 from the layer containing moisture sensor 144 as depicted in the figure).

In some embodiments, the removable pad 140 can be separated from the garment 104B, the garment 104B (whether underwear, shorts or other garment), being fit to the user's body to keep the EMG sensors 142 close to and in as full contact as possible with the wearer's skin. Alternatively, the consumable component could be permanently integrated into the garment, e.g., a disposable or reusable undergarment.

"Electromyography" or "EMG" is an electrodiagnostic medicine technique for evaluating and recording the electrical activity produced by skeletal muscles. EMG is performed using an electromyograph and produces a record called an electromyogram. An electromyograph detects the electric potential generated by muscle cells when these cells are electrically or neurologically activated. The signals can be analyzed to detect medical abnormalities, activation level, or recruitment order, or to analyze the biomechanics of a person's movement. In the wearable pelvic floor muscle therapy system, a surface EMG assesses muscle function by recording muscle activity from the skin surface above the muscle.

Surface EMGs such as the EMG sensors 142 can be recorded by a pair of electrodes or by a more complex array of multiple electrodes. More than one electrode is needed, because EMG recordings display the potential difference (voltage difference) between two separate electrodes. Muscle tissue at rest is normally electrically inactive. The muscle at rest should be electrically quiet, and when the muscle is voluntarily contracted action potentials begin to appear. As the strength of the muscle contraction is increased, more and more muscle fibers produce action potentials. When the muscle is fully contracted, there should appear a disorderly group of action potentials of varying rates and amplitudes (a complete recruitment and interference pattern), which is detected and monitored by the sensors described herein.

In noninvasive systems 120 and 150, the EMG sensors 142 are positioned on removable pad 140 so that when fit with respective garment 104A, 104B and worn, the EMG sensors 142 come near or into contact with the pelvic muscles of the male or female user, respectively.

The moisture sensors 144 that can be included in noninvasive sensors 102 detect both volume and the number of times liquid is present. Previous liquid control systems (e.g., bedwetting systems), are binary and indicate if a sensor and thus the material attached to the sensor is wet or dry. The moisture sensors 144 advantageously measure actual fluid volumes instead of providing a simple dry/wet indication. Current moisture volume calculation methods for incontinence involve patients weighing soaked pads or diapers, and estimating liquid content from the weight. The moisture sensors 144 advantageously calculate the liquid volume present without a need for weighting. An advantageous sensing method is to use a transmission line dielectric impedance system. Such a system relies on the amount of time it takes a signal to move down a line and back, which changes due to a level of moisture present in the dielectric. Measurement of the change in capacitance of advantageously allows volume present to be calculated. Such volume sensing has been previously used in fields wholly unrelated to incontinence treatment, such as soil and snow sensing for agricultural and weather prediction purposes. The moisture sensors 144 thus allow for precise measurement of liquid volumes for incontinence patients.

The moisture sensors 144 are able to detect whether liquid is present and how much. The moisture sensors 144 can also determine how quickly the moisture is produced (as it tracks change of volume over time). Since urination is much more rapid than sweating, the software 130 filters out any moisture detected as being sweat and reports on moisture provided only by voiding.

Additionally, the system can include an accelerometer to detect the wearer's motion. Such an accelerometer can be included in module 122, for example. If motion such as biking or running is detected, the system can include the information that the wearer is exercising and account for the increase in produced sweat on the incontinence measurement. The system may also include a humidity sensor.

Figure 4A:
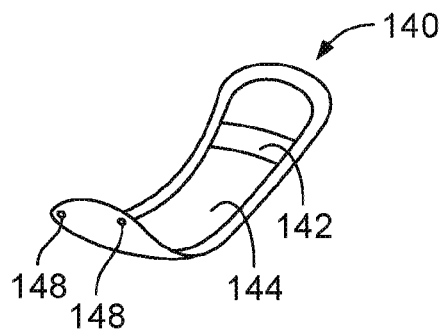
FIGS. 4A and 4B are schematic diagrams that show details of wearable sensor pads for use with the systems shown in FIGS. 1, 2, and 3.
Figure 4B:
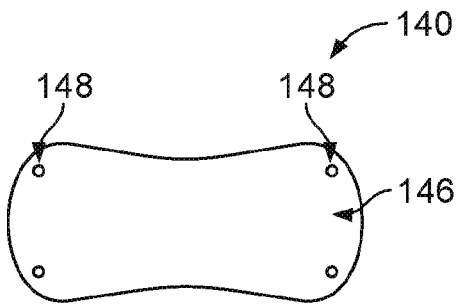

FIGS. 4A and 4B show isometric and rear views of an embodiment of removable pad 140. In this embodiment, EMG sensors 142 and moisture sensors 144 attached to a substrate 146 that is absorbent. The rear of the substrate 146 has snaps 148 that can be used to attach the removable pad 140 to the garment 104. Wiring runs from the snaps 148 to the insertable radio module 122, carrying the signals of the sensors. Alternatively, adhesive can attach the rear of substrate to the garment, rather than snaps.

Figure 5A:
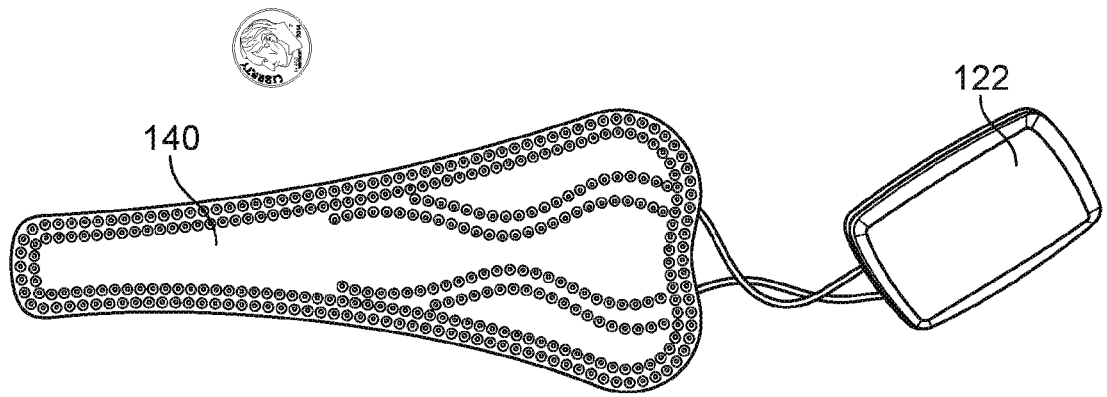
FIGS. 5A and 5B are two examples of wearable sensor pads with reusable modules for use with the systems shown in FIGS. 1, 2, and 3.
Figure 5B:
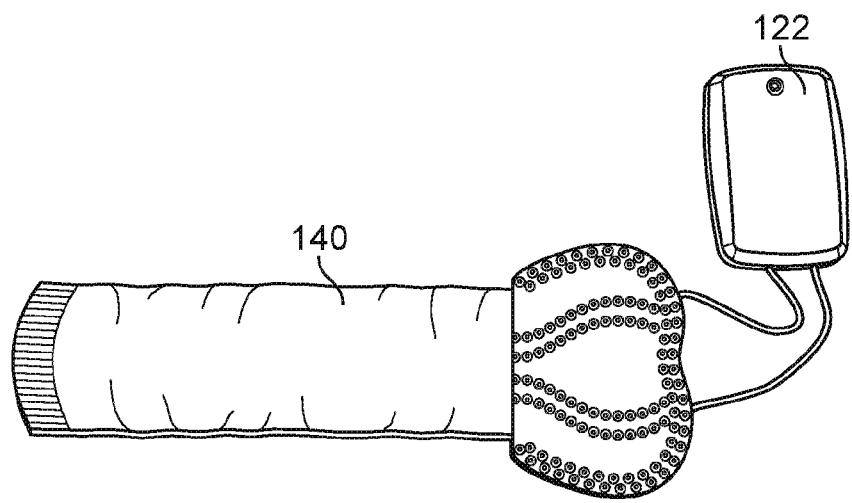

Two possible embodiments of removable pad 140 and module 122 are shown in FIGS. 5A and 5B.

FIGS. 6A-D show an embodiment of portions of a non-invasive system 200, with removable pad 240 connected to a module 222 by wires 260. The removable pad 240 includes an absorbent layer 246 integrated with a moisture sensor 244. EMG sensors 242 are attached to an EMG layer 250 via contacts 252 (e.g., snaps that are electrically conductive). The EMG layer 250 can lie underneath the absorbent and moisture sensor layer 244, 246. The EMG layer could alternatively lie above the absorbent layer 246 and moisture sensor 244. The EMG layer 250, absorbent layer 246 and moisture sensor 244 can be combined or rearranged in any order. Placing the combined moisture sensor 244 and absorbent layer 246 on top and closest to the urine source when worn is particularly advantageous. The EMG layer 250 can also advantageously extend beyond the moisture sensor 244 and absorbent layer 246, placing the EMG sensors 242 closer to the muscles and in direct contact with the wearer's skin and simultaneously separated from the urine.

Figure 6A:
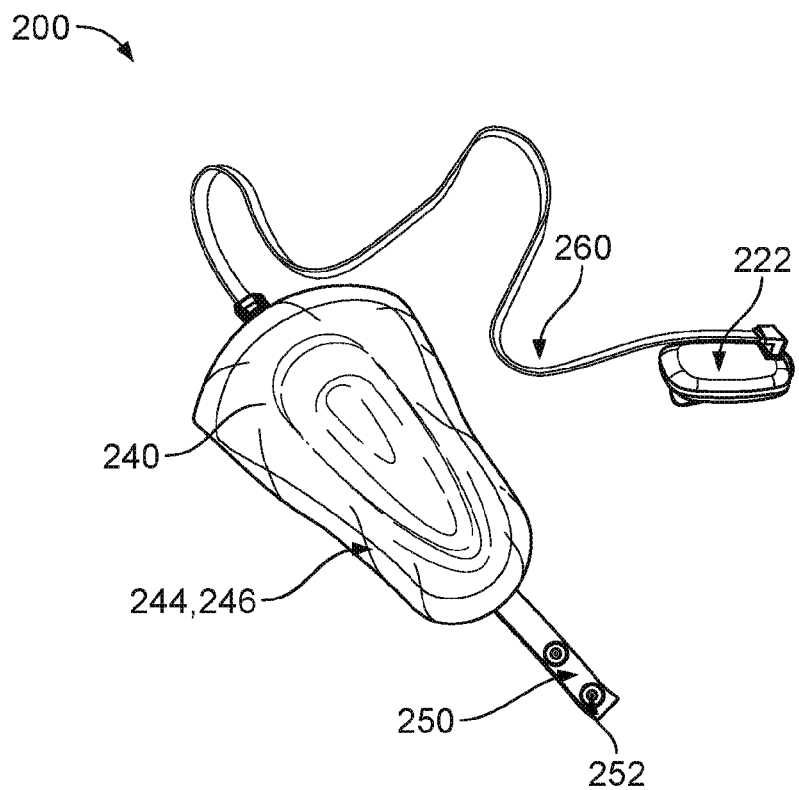
FIGS. 6A-6D are examples of components of an additional embodiment of wearable sensor pads with reusable modules for use with the systems shown in FIGS. 1, 2, and 3.
Figure 6B:
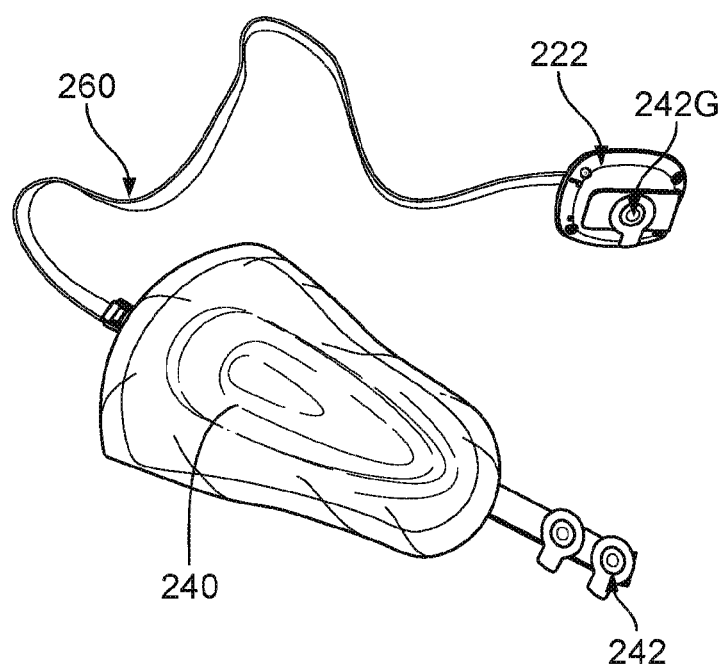
Figure 6C:
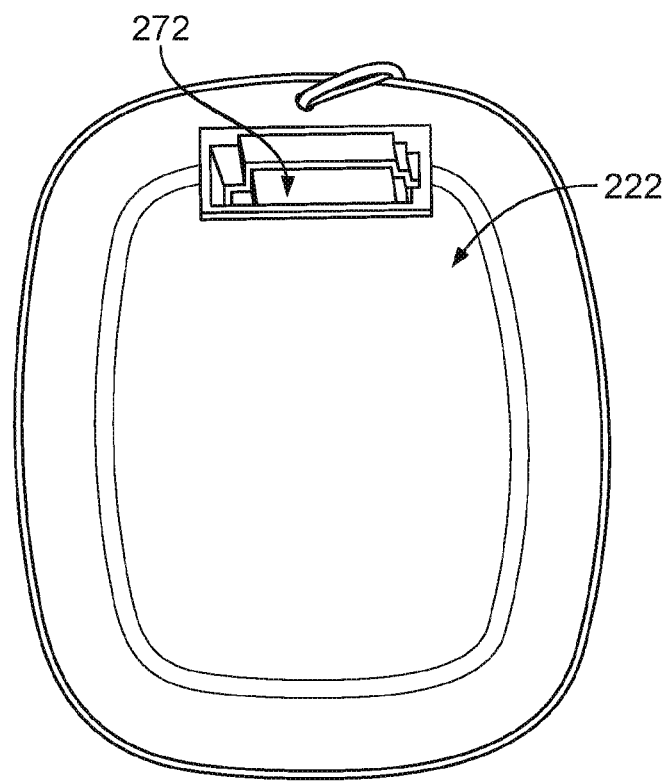
Figure 6D:
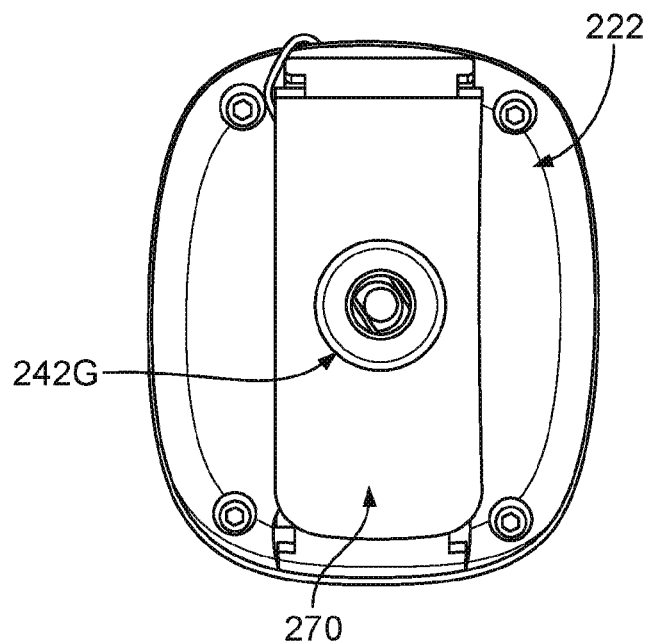

As shown in FIGS. 6B and 6D, an EMG sensor 242G is also included on the back of the module 222. This EMG sensor 242G that is mounted to the module 222 can serve as a ground. Specifically, EMG sensor 242G is mounted to a clip 270 on the back of the module 222. The clip 270 allows the module 222 to attach to a user's undergarment such as at the waistband. In such an arrangement, the EMG sensor 242G conveniently presses against the user's abdominal wall, providing a ground for the EMG readings. The module 222 also includes port 272 for wires 260 that conduct signals from the moisture sensor 244 and the EMG sensors 242.

Figure 7:
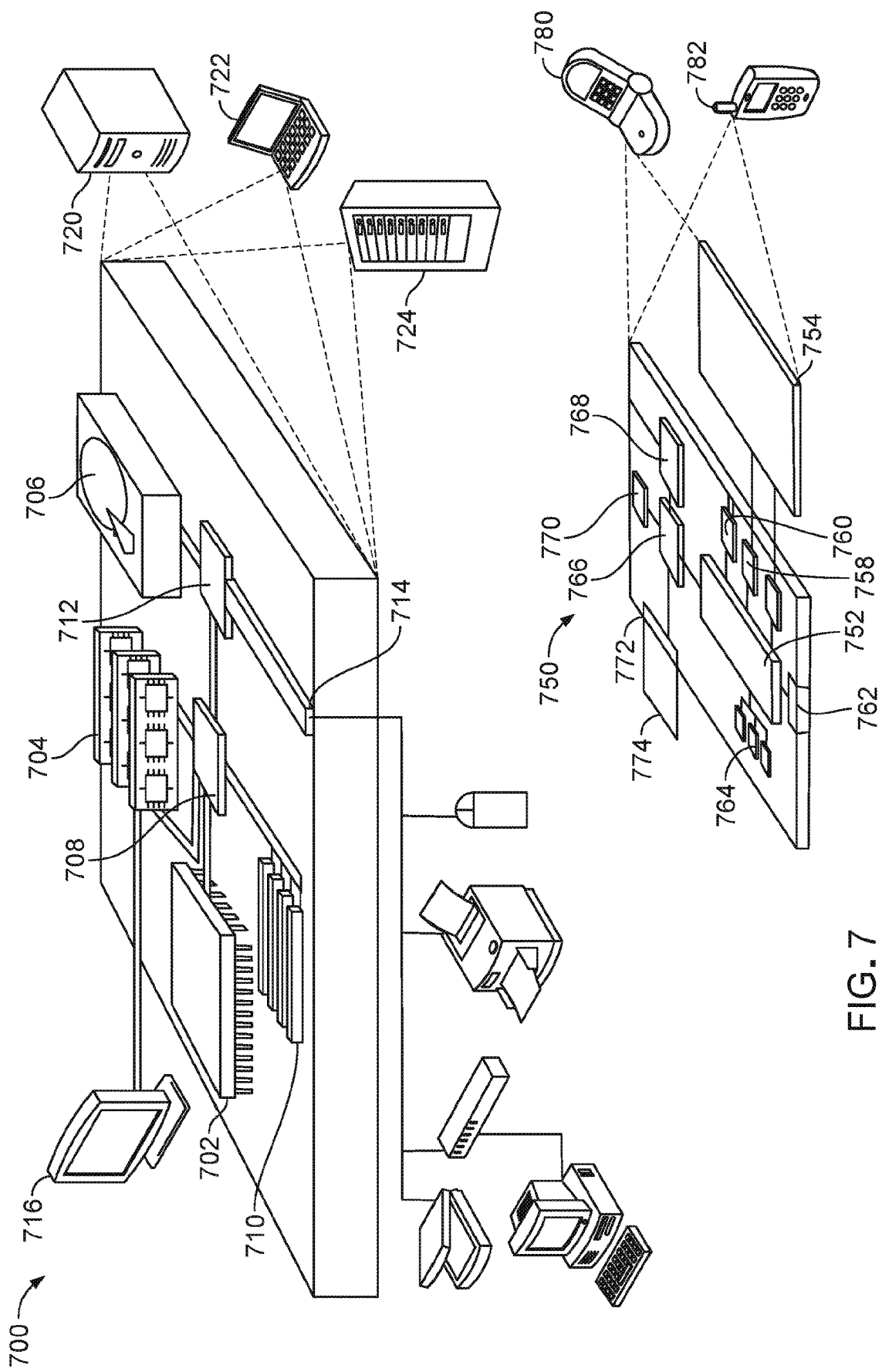
FIG. 7 is a schematic diagram that illustrates an example of a computing device and a mobile computing device that can be used to implement the techniques described here.

FIG. 7 shows an example of a general computing device 700 and an example of a mobile computing device 750, which can be used to process user-related information obtained from sensors 102 as described herein and to implement the techniques described herein.

Computing device 700 is intended to represent various forms of digital computers, including, e.g., laptops, desktops, workstations, personal digital assistants, servers, blade servers, mainframes, and other appropriate computers. Computing device 750 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 700 includes processor 702, memory 704, storage device 706, high-speed interface 708 connecting to memory 704 and high-speed expansion ports 710, and low speed interface 712 connecting to low speed bus 714 and storage device 706. Each of components 702, 704, 706, 708, 710, and 712, are interconnected using various busses, and can be mounted on a common motherboard or in other known manners as appropriate. Processor 702 can process instructions for execution within computing device 700, including instructions stored in memory 704 or on storage device 706 to display graphical data for a GUI on an external input/output device, including, e.g., display 716 coupled to high speed interface 708. In other implementations, multiple processors and/or multiple buses can be used, as appropriate, along with multiple memories and types of memory. Also, multiple computing devices 700 can be connected, with each device providing portions of the necessary operations (e.g., as a server bank, a group of blade servers, or a multi-processor system).

Memory 704 stores data within computing device 700. In one implementation, memory 704 is a volatile memory unit or units. In another implementation, memory 704 is a non-volatile memory unit or units. Memory 704 also can be another form of computer-readable medium, including, e.g., a magnetic or optical disk. Memory 704 can be tangible and non-transitory.

Storage device 706 is capable of providing mass storage for computing device 700. In one implementation, storage device 706 can be or contain a computer-readable medium, including, e.g., a floppy disk device, a hard disk device, an optical disk device, or a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 704, storage device 706, memory on processor 702, and the like.

High-speed controller 708 manages bandwidth-intensive operations for computing device 700, while low speed controller 712 manages lower bandwidth-intensive operations. Such allocation of functions is an example only. In one implementation, high-speed controller 708 is coupled to memory 704, display 716 (e.g., through a graphics processor or accelerator), and to high-speed expansion ports 710, which can accept various expansion cards (not shown). In the implementation, low-speed controller 712 is coupled to storage device 706 and low-speed expansion port 714. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router, e.g., through a network adapter.

Computing device 700 can be implemented in a number of different forms, as shown in the figure. For example, it can be implemented as standard server 720, or multiple times in a group of such servers. It also can be implemented as part of rack server system 724. In addition or as an alternative, it can be implemented in a personal computer including, e.g., laptop computer 722. In some examples, components from computing device 700 can be combined with other components in a mobile device (not shown), including, e.g., device 750. Each of such devices can contain one or more of computing device 700, 750, and an entire system can be made up of multiple computing devices 700, 750 communicating with each other.

Computing device 750 includes processor 752, memory 764, an input/output device including, e.g., display 754, communication interface 766, and transceiver 768, among other components. Device 750 also can be provided with a storage device, including, e.g., a micro-drive or other device, to provide additional storage. Each of components 750, 752, 764, 754, 766, and 768, are interconnected using various buses, and several of the components can be mounted on a common motherboard or in other manners as appropriate.

Processor 752 can execute instructions within computing device 750, including instructions stored in memory 764. The processor can be implemented as a chipset of chips that include separate and multiple analog and digital processors. The processor can provide, for example, for coordination of the other components of device 750, including, e.g., control of user interfaces, applications run by device 750, and wireless communication by device 750.

Processor 752 can communicate with a user through control interface 758 and display interface 656 coupled to display 754. Display 754 can be, for example, a TFT LCD (Thin-Film-Transistor Liquid Crystal Display) or an OLED (Organic Light Emitting Diode) display, or other appropriate display technology. Display interface 656 can comprise appropriate circuitry for driving display 754 to present graphical and other data to a user. Control interface 758 can receive commands from a user and convert them for submission to processor 752. In addition, external interface 762 can communicate with processor 642, so as to enable near area communication of device 750 with other devices. External interface 762 can provide, for example, for wired communication in some implementations, or for wireless communication in other implementations, and multiple interfaces also can be used.

Memory 764 stores data within computing device 750. Memory 764 can be implemented as one or more of a computer-readable medium or media, a volatile memory unit or units, or a non-volatile memory unit or units. Expansion memory 774 also can be provided and connected to device 750 through expansion interface 772, which can include, for example, a SIMM (Single In Line Memory Module) card interface. Such expansion memory 774 can provide extra storage space for device 750, or also can store applications or other data for device 750. Specifically, expansion memory 774 can include instructions to carry out or supplement the processes described above, and can include secure data also. Thus, for example, expansion memory 774 can be provided as a security module for device 750, and can be programmed with instructions that permit secure use of device 750. In addition, secure applications can be provided through the SIMM cards, along with additional data, including, e.g., placing identifying data on the SIMM card in a non-hackable manner.

The memory can include, for example, flash memory and/or NVRAM memory, as discussed below. In one implementation, a computer program product is tangibly embodied in a data carrier. The computer program product contains instructions that, when executed, perform one or more methods, including, e.g., those described above. The data carrier is a computer- or machine-readable medium, including, e.g., memory 764, expansion memory 774, and/or memory on processor 752, which can be received, for example, over transceiver 768 or external interface 762.

Device 750 can communicate wirelessly through communication interface 766, which can include digital signal processing circuitry where necessary. Communication interface 766 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 768. In addition, short-range communication can occur, including, e.g., using a Bluetooth®, WiFi, or other such transceiver (not shown). In addition, GPS (Global Positioning System) receiver module 670 can provide additional navigation- and location-related wireless data to device 750, which can be used as appropriate by applications running on device 750. Sensors and modules such as compasses and accelerators (for orientation sensing), etc. maybe included in the device.

Device 750 also can communicate audibly using audio codec 760, which can receive spoken data from a user and convert it to usable digital data. Audio codec 760 can likewise generate audible sound for a user, including, e.g., through a speaker, e.g., in a handset of device 750. Such sound can include sound from voice telephone calls, can include recorded sound (e.g., voice messages, music files, and the like) and also can include sound generated by applications operating on device 750.

Computing device 750 can be implemented in a number of different forms, as shown in the figure. For example, it can be implemented as cellular telephone 780. It also can be implemented as part of smartphone 782, personal digital assistant (PDA), or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, such a software application 130 (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube)

or LCD (liquid crystal display) monitor) for displaying data to the user and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a user interface or a Web browser through which a user can interact with an implementation of the systems and techniques described here), or a combination of such back end, middleware, or front end components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

Methods of Using a Noninvasive Wearable Pelvic System

The noninvasive wearable system 100 integrates office data with in-home data to allow more frequent data collection and hence more effective care. The combination of wearable superficial sensors 142 and 144 and a user application 130 allow users and healthcare providers to assess, track, and record patient progress with noninvasive wearable system 100.

The noninvasive wearable system 100 includes a data storage (e.g., memory 704, 764) so that a doctor can see a user's exercise history (for example, over the past one or two weeks or since the previous doctor visit) as detected by the EMG sensors. This allows the doctor to monitor whether the user has been keeping up with the exercise regimen, and whether the user has been doing the exercises properly. This determination is particularly advantageous, because it more accurately allows the healthcare provider to determine whether this type of non-invasive treatment is being implemented correctly before moving on to a more invasive treatment such as surgery.

The feedback can be either stored on the device, and/or fed via wireless connectivity (or a plug-in option) to the user's healthcare provider's office in real time. The office can keep a record of the sensor data, or in the case of the memory stored on the device the user can send or give the data to the healthcare provider.

The feedback can flow over a network to be accessed by the user later for review and also can be accessed by clinicians for remote diagnosis and/or storage.

The system gives direct, personal feedback to the user at home. The user can know in real time if he or she is performing the exercises correctly. In some instances, the system can prompt the user as to how to change the exercises to improve their effectiveness. This feedback will be provided by the software application 130, e.g., through the user's personal mobile telephone 106 or other device.

The devices are ideally suited to replace time-consuming and costly in-clinic treatments. Although providing the functionality of a hospital-based monitor the system described herein allows the user to be better monitored and coached in performing the exercise regimen determined by the healthcare professional.

In addition, users' data may be applied to machine learning algorithms to provide custom individualized coaching programs.

The invention is further described in the following example describing a specific embodiment, which does not limit the scope of the invention described in the claims.

EXAMPLES

Figure 8:
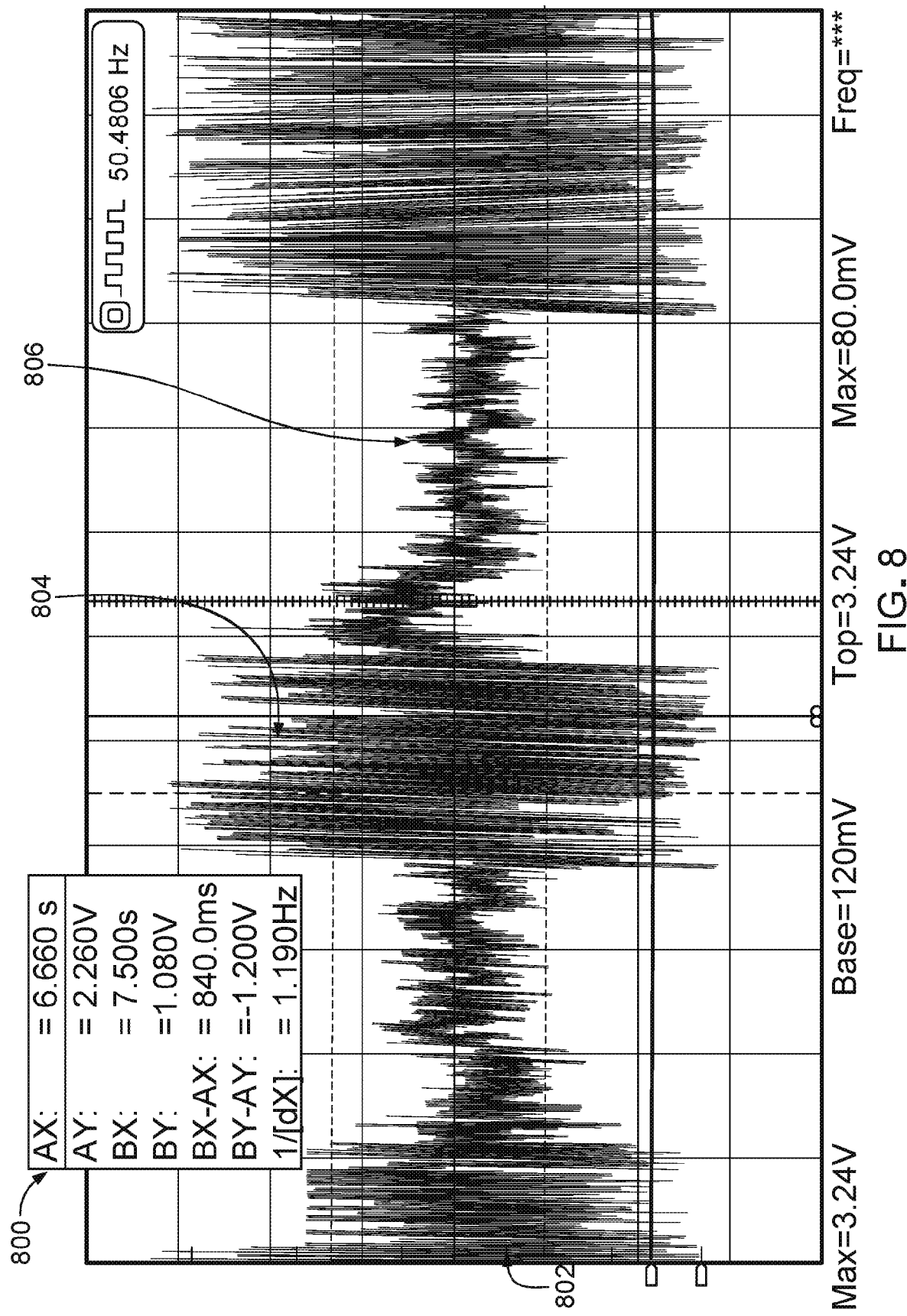
FIG. 8 is an example of an oscilloscope trace image obtained from testing of an EMG sensor that can be used with the systems described herein.
Figure 9:
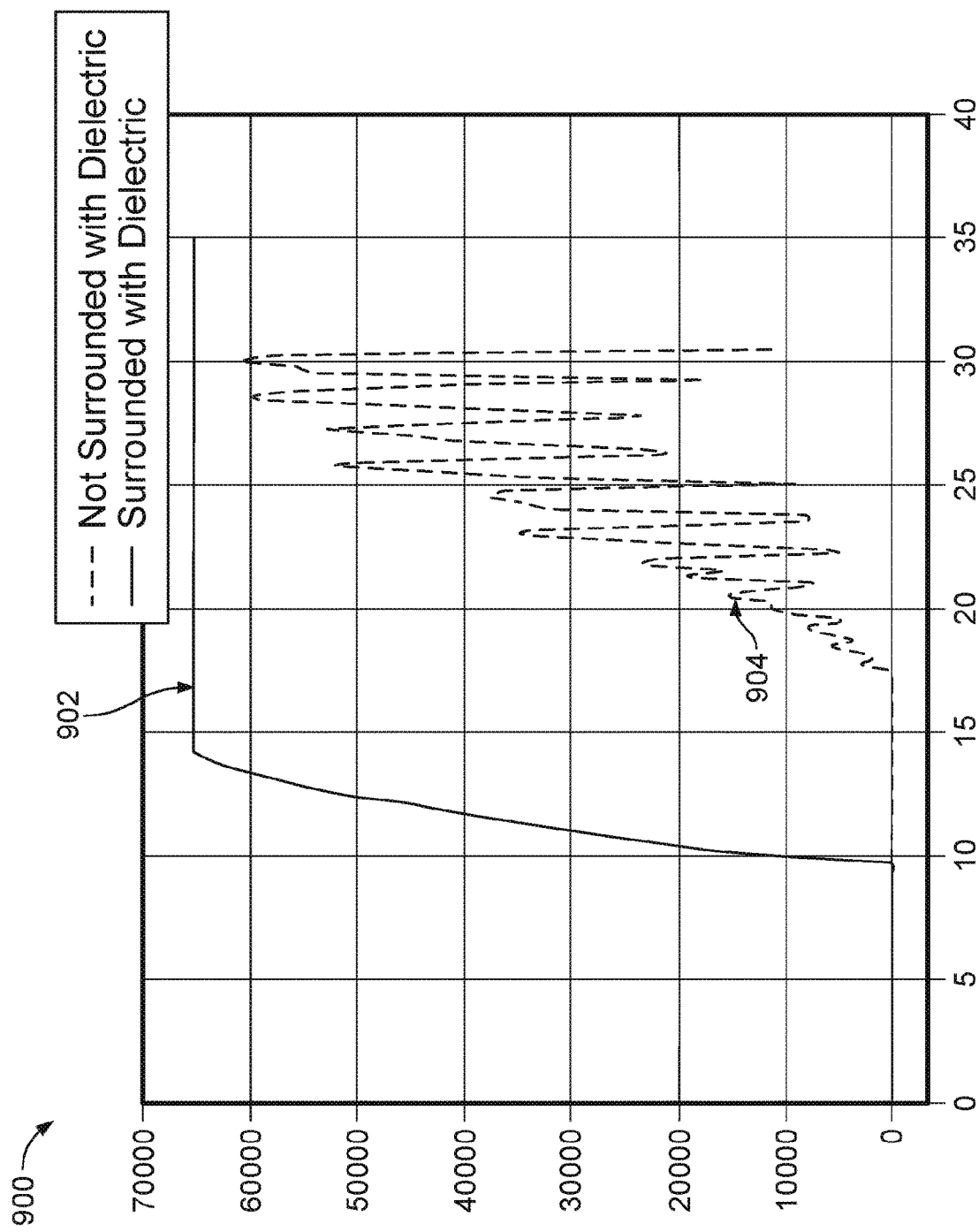
FIG. 9 is a graph demonstrating the effect of saturation on the dielectric constant of a moisture sensor that can be used with the systems described herein.

The examples of the specific implementations illustrated in FIGS. 8 and 9 output EMG and moisture data directly to a user's smartphone via a Bluetooth Low Energy wireless interface, though other forms of wireless communication can also be used.

FIG. 8 shows an example of display 800 a specific oscilloscope trace 802 obtained from a system using an EMG sensor. In this example, an EMG circuit for use in the wearable devices described herein is designed to pass EMG signals in a frequency range of ~25 Hz to ~630 Hz. The gain of the unit is electrically programmable from 5 to 500 to allow for a wide range of electrical signal strength.

The display 800 shows the EMG output or trace 802 over time when surface electrodes are attached to a user's body over a major muscle group such as the pelvic floor muscles. In these data, the rest period is as a <750 mVp-p signal and the activated muscle signal period is displayed as a ~3 Vp-p signal. The gain stages are electronically adjustable and will be calibrated when the system is attached to the user, and the signals are usable for analog-to-digital readout.

The trace 802 shows zones of high amplitude 804 and low amplitude 806 of measured electrical potential. High amplitude zone 804 corresponding to muscle contraction and low amplitude 806 is when the muscles are relaxed. The stronger the user contracts the measured muscles, the higher the amplitude of the high amplitude zones 804, and the longer the user contracts the muscles the wider is the zone of high amplitude. The user (or a clinician) can review the saved data for changes over time (e.g., higher amplitude indicating stronger muscles, or longer period of contraction indicating increases in stamina).

Traces such as trace 802 shown is beneficial to track a patient's PFMT exercises as part of noninvasive system 100. Such data is useful for all patients engaged in a PFMT regimen, such as men prior to prostate surgery (who wish to reduce or minimize incontinence), pregnant women strengthening their vaginal muscles, and both men and women treat with sexual dysfunction. Noninvasive wearable system 100 including EMG sensors 242 is beneficial to such patients.

FIG. 9 is an example graph 900 of capacitance over time measured by one implementation of a capacitive moisture sensor that can be used with the devices described herein. The moisture sensor is capable of measuring capacitance of up to 4 pF with a maximum offset of 10 pF.

A waterproof sensor was designed to generate different measured capacitances due to a change in relative permeability of an absorbent material. The example sensor was made of two pieces of copper foil, silicone, polyimide tape, and an absorbent material, e.g., similar to the material found in incontinence pads. The flexible copper plates were trimmed to an area of 12.7 mm by 55 mm, soldered to wire leads, and covered in waterproof silicone and polyimide tape. The plates were aligned to one another in parallel and separated with the absorbent material by 7-10 mm. The capacitor was also wrapped in a layer of the absorbent material to minimize the effect of human body capacitance in moisture measurement.

When the absorbent medium becomes saturated with moisture, the dielectric constant increases drastically. In graph 900 of capacitance over time, the x axis is liquid volume, and y axis is capacitance measured by the moisture sensor. When directly exposed to water when testing the moisture sensor either with (the upper trace 902) or without (the lower trace 904) a surrounding dielectric, the effect of moisture saturation is shown by the increased slope of the trace. Such a change is quite clear even when the sensor was nestled in a tester's groin. The upper trace 902 shows a fairly clear slope, while a line can be fit to the lower trace 904 and a slope found from the fitted line. The rate of change of the measured capacitance is related to the rate of change in fluid volume, giving the amount of urine in the pad. The relationship between measured capacitance and volume can be calibrated beforehand, or calculated by knowing the thickness, material, etc. of the layers in the pad.

A noninvasive wearable system 100 including such a moisture sensor can be useful in diagnosing and treating patients with urinary incontinence.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A wearable device to enhance pelvic floor muscle therapy (PFMT), the device comprising:
   an electromyograph (EMG) sensor arranged within a garment to measure contraction of a pelvic floor muscle of a wearer of the garment; and
   a moisture sensor arranged within the garment for measuring a volume of urine voided by the wearer as a function of time;
   wherein higher amplitude signals from the EMG sensor over time indicates stronger pelvic floor muscles and a wider zone of the high amplitude signals from the EMG sensor over time indicates an increase in stamina in performing PFMT; and
   wherein an indication of stronger pelvic floor muscles, an increase in stamina in performing PFMT, or both, indicate an improvement in PFMT exercises over time.

2. The device of claim 1, wherein the EMG sensor and moisture sensor are attached to a substrate.

3. A system to enhance pelvic floor muscle therapy (PFMT), the system comprising:
   a wearable device of claim 1 associated with an individual user; and
   a display device that receives data from the wearable device.

4. The system of claim 3, wherein the wearable device comprises a reusable component.

5. The system of claim 4, wherein the reusable component includes a Bluetooth® wireless sensor and wires attached to the Bluetooth® wireless sensor.

6. The system of claim 5, wherein the wires electrically connect the EMG sensor and the moisture sensor to the Bluetooth® wireless sensor.

7. The system of claim 4, wherein the reusable component comprises underwear, a diaper, or shorts.

8. The system of claim 4, wherein the reusable component is removably attachable to the garment.

9. The system of claim 3, wherein the wearable device comprises a consumable component.

10. The system of claim 9, wherein the consumable component includes an absorbent component.

11. The system of claim 3, wherein the system further comprises a software application configured to automatically receive data communicated from the wearable device and to display data to the user on the display device.

12. The system of claim 11, wherein the software application is further configured to automatically send and receive data to and from an external system.

13. A method of enhancing pelvic floor muscle therapy (PFMT), the method comprising:
    providing a disposable component comprising an electromyograph (EMG) sensor configured to measure contraction of a pelvic floor muscle of a wearer of the disposable component and a moisture sensor arranged in the disposable component for measuring a volume of urine voided by the wearer as a function of time;
    detecting a signal from the EMG sensor and a signal from the moisture sensor;
    saving an output based on the signal from the EMG sensor and the moisture sensor; and
    using the output to provide real time feedback to a user on a level of improvement in PFMT exercises over time;
    wherein higher amplitude signals from the EMG sensor over time indicates stronger pelvic floor muscles and a wider zone of the high amplitude signals from the EMG sensor over time indicates an increase in stamina in performing PFMT; and
    wherein an indication of stronger pelvic floor muscles, an increase in stamina in performing PFMT, or both, indicate an improvement in PFMT exercises over time.

14. The method of claim 13, wherein the output comprises a number of incontinence episodes detected.

15. The method of claim 13, wherein the output comprises a volume of fluid detected.

16. The method of claim 13, further comprising displaying the output on a screen.

17. The method of claim 16, wherein the screen is a smart phone, laptop, or computer monitor.

18. The method of claim 13, comprising sending the signals to an external system.

19. A method of diagnosing, treating, and/or managing weak pelvic floor muscles in a patient, the method comprising:
    providing a disposable component comprising an electromyograph (EMG) sensor and configured to be attached to a garment that when worn places the EMG sensor into a position on the patient's skin that enables the EMG to measure contraction of a pelvic floor muscle of the patient;
    providing a moisture sensor arranged in the disposable component for measuring a volume of urine voided by the wearer as a function of time;
    detecting a signal from the EMG sensor; and
    saving an output based on the signal from the EMG sensor and/or the moisture sensor; and using the output to provide real time feedback to a user on a level of improvement in weak pelvic floor muscles over time;

wherein higher amplitude signals from the EMG sensor over time indicates stronger pelvic floor muscles and a wider zone of the high amplitude signals from the EMG sensor over time indicates an increase in stamina in pelvic floor muscles; and wherein an indication of stronger pelvic floor muscles, an increase in stamina in pelvic floor muscles, or both, indicate an improvement in weak pelvic floor muscles over time.

20. The method of claim 19, further comprising displaying the output on a display device.

* * * * *